United States Patent [19]

Staveski et al.

[11] Patent Number: 5,354,853
[45] Date of Patent: Oct. 11, 1994

[54] PHOSPHOLIPID-SACCHARIDE CONJUGATES

[75] Inventors: Mark M. Staveski, Sharon; Barbara Y. F. Wan, Tewksbury; Alan E. Walts, Topsfield, all of Mass.

[73] Assignee: Genzyme Corporation, Cambridge, Mass.

[21] Appl. No.: 30,793

[22] Filed: Mar. 12, 1993

[51] Int. Cl.$^5$ .................. C12P 19/44; C07H 15/00; C07G 3/00
[52] U.S. Cl. .................. 536/17.1; 435/74; 536/4.1; 536/124
[58] Field of Search .......... 536/4.1, 17.1, 124; 435/74

[56] References Cited

U.S. PATENT DOCUMENTS 4,624,919 11/1986 Kokusho et al. .............. 435/74

OTHER PUBLICATIONS

Boeckel et al [I] Tetrahedron vol. 37, No. 21, pp. 3751–3761 (1981).
Boeckel et al [II] Tet. Lt. No. 37, pp. 3561–3564 1979.
Gurr et al Biochem J. (1968) 108, 211.
ASTN ABS of CA 119(15):158396v Ri et al JP 05132496 May, 28, 1993.
P. W. Tang, et al. "Novel Approach to Study of the Antigenicities and Receptor Functions of Carbohydrate Chains of Glycoproteins", *Biochemical and Biophysical Research Communications*, 132, No. 2: 474–480 (1985).
Haensler, et al. "Influence of the galactosyl ligand structure on the interaction of galaosylated liposomes with mouse peritoneal macrophages", *Glycoconjugate Journal*, 8: 116–124 (1991).
Weissig, et al. "Covalent coupling of sugars to liposomes", *Biochimica et Biophysica Acta*, 1003: 54–57 (1989).
Singh, et al. "Phosphatidylhydroxyalkanols as Versatile Intermediates in the Synthesis of Headgroup Modified Diacetylenic Phospholipids", *Synthetic Communications*, 22(16): 2293–2304 (1992).

*Primary Examiner*—Herbert J. Lilling
*Attorney, Agent, or Firm*—William G. Gosz

[57] ABSTRACT

Novel phospholipid-saccharide conjugates are produced by the reaction of a phospholipid derivative and an activated saccharide. The resulting conjugates can be used to make liposomes which are target-specific or resistant to degradation in vivo.

18 Claims, No Drawings

PHOSPHOLIPID-SACCHARIDE CONJUGATES

BACKGROUND OF THE INVENTION

Phospholipids are a naturally-occurring class of compounds which have been shown to be involved in various cellular functions. For example, phospholipids are integral components of cell membranes and lung surfactants, and play a major role in intracellular and extracellular signal transduction and cellular inflammatory pathways.

Phospholipids typically are composed of a glycerol backbone which is acylated with fatty acids at the $C_1$ and $C_2$ positions and phosphorylated at the remaining terminus. The fatty acids may or may not be identical, and may vary in degree of saturation. In one subclass of phospholipids, termed ether phospholipids, an ether linkage with an aliphatic chain is formed at the $C_1$ position. Phospholipids also may be esterified with "head groups" on the phosphate moiety. Some commonly occurring head groups include ethanolamine (phosphatidylethanolamine), choline (phosphatidylcholine), glycerol (phosphatidylglycerol), serine (phosphatidylserine) and inositol (phosphatidylinositol).

Various protocols for synthesizing phospholipid-saccharide conjugates have been published in the literature. The traditional approach is to combine phosphatidylethanolamine with a reducing saccharide to form an imine, which is then reduced by sodium cyanoborohydride to give a stable amino linkage (P. W. Tang et al. (1985) *Biochem. Biophys. Res. Comm.*, 132:474–480). However, reductive amination destroys the ring structure of the reducing terminus of the saccharide, which may lead to changes in the biological activity of resultant phospholipid-saccharide conjugates. Phospholipid-saccharide conjugates have also been prepared enzymatically. For example, Phospholipase-D enzymes isolated from various organisms including Streptomyces (S. Shuto, S. Imamura, K. Fukukawa, T. Ueda (1988) *Chem. Pharm. Bull.*, 36: 5020–5023), Actinomedura and Nocardiopsis (Y. Kokusho et al., U.S. Pat. No. 4,624,919, issued Nov. 25, 1986) have been demonstrated to catalyze the transfer of a phosphatidyl residue from phosphatidylcholines to a primary hydroxy group of the saccharide. However, this method precludes any modification of the distance between the phospholipid and the saccharide. As a result, the accessibility of the saccharide residues may be limited sterically when the phospholipid-saccharide conjugates are incorporated into liposomes.

The chemical synthesis of phospholipid-galactose conjugates has been reported (J. Haensler et al. (1991) *Glycoconjugate J.*, 8: 116–124). The synthetic scheme involves preparing 2'-carboxyethyl-1-thiogalactoside in four steps from commercially available peracetylated galactose. The carboxylic acid on the galactoside is further refunctionalized with 1,3-diamino-2-propanol via amidation. The derivatized galactose is then coupled to the N-hydroxysuccinimide ester of N-succinyl phosphatidylethanolamine. As described in the report, the linker between the phospholipid and the galactose in the final product contains a minimum of sixteen C—C, C—O and C—N bonds. This procedure is not suitable if conjugates having a shorter linker are desired.

Phospholipids have been used extensively as components for liposomes. Liposomes are lipid vesicles which can be used to encapsulate and deliver drugs to cell tissues. Conventional liposomes, however, are rapidly cleared from the bloodstream by the reticuloendothelial system (RES). In order to improve the targeting capabilities of the liposomes, second generation liposomes have been constructed. These improved liposomes generally can be catagorized into two types: one type has an extended circulatory lifetime, the other type has the ability to target specific tissues via cellular interactions between the liposome and the target cell.

Phospholipids modified with saccharides have been utilized in preparing both types of liposomes. For example, liposomes containing $G_{M1}$ have been shown to exhibit the ability to avoid RES uptake, though the mechanism of avoidance is not yet well understood. Liposomes composed of $G_{M1}$-distearoylphosphatidylcholine-cholesterol, when compared to formulations containing combinations of phosphatidylserine, phosphatidylcholine and cholesterol, show high levels of accumulation in blood and concommitant low levels in liver and spleen (A. Gabison, D. Papahadjopoulos (1988) *Proc. Natl Acad. Sci.*, 85:6949–6953). Ligand-receptor interactions have been used to construct liposomes targeted to specific cell tissues. For example, mannosylated phosphatidylinositols, which are extracted from the cell wall of mycobacteria, have been incorporated in liposomal systems and shown to be effective in delivering therapeutic agents to macrophages via the cell-surface mannose receptors (G. Barratt et al. (1986) *Biochim. Biophys. Acta*, 862:153–164). Liposomes containing p-aminophenyl mannoside were reported to enhance the transport mechanism across the blood-brain barrier (F. Umezawa, Y. Eto (1988) *Biochem. & Biophys. Res. Comm.*, 153:1038–1044). Vesicles containing conjugates of cholesterol with 6-amino-6-deoxy-mannoside show significant ability to enhance the uptake of the vesicles by mouse peritoneal macrophages, where receptors for mannose-terminated glycoprotein are located (P.-S. Wu, G. W. Tin, J. Baldeschwieler (1981) *Proc. Natl. Acad. Sci. U.S.A.*, 78:2033–2037). Haensler and F. Schuba (*Biochim. Biophys. Acta*, 946:95–105 (1988)) describe galactosylated liposomes. They report that results from studies directed toward the interaction of these liposomes with mouse peritoneal macrophages show a 4- to 5-fold increase in binding of the liposomes to the cells.

None of the liposomes heretofore described display effective levels of tissue specificity and resistance to degradation in vivo, however. Phospholipid-sugar conjugates which could be used to make cell-targeted liposomes or which are resistant to RES uptake would be useful.

SUMMARY OF THE INVENTION

The invention relates to phospholipid-saccharide conjugates comprising a phospholipid moiety and a saccharide moiety joined by a diether linker, having the general formula:

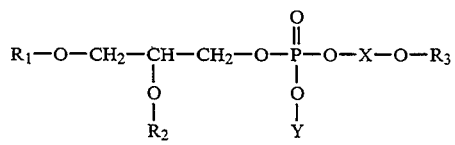

wherein $R_1$ and $R_2$ independently comprise alkyl, substituted alkyl, alkenyl, substituted alkenyl, alkynyl, substituted alkynyl, aryl, substituted aryl, arylalkyl, substituted arylalkyl, or C(O)R wherein R represents alkyl, substituted alkyl, alkenyl, substituted alkenyl, alkynyl, substituted alkynyl, aryl, substituted aryl, arylalkyl and substituted arylalkyl;

Y comprises a cationic moiety including a hydrogen ion, alkali metal ions, alkali earth metal ions, an ammonium ion, and substituted ammonium ions;

X comprises alkyl, substituted alkyl, alkenyl, substituted alkenyl, alkynyl, substituted alkynyl, aryl, substituted aryl, arylalkyl and substituted arylalkyl; and $R_3$ comprises a saccharide moiety.

$R_1$ and $R_2$ preferably are fatty acid residues such as, for example, stearoyl, palmitoyl, linolenoyl, myristoyl, dodecanoyl, oleoyl or linoleoyl. $R_1$ and $R_2$ may be the same or different fatty acid residues. Y preferably is a cation. X preferably is a straight chain or branched alkyl having from about 1 to about 20 carbon atoms. $R_3$ preferably is a monosaccharide, dissacharide, oligosaccharide or polysaccharide consisting essentially of, for example, the following saccharides: mannose, galactose, glucose, lactose or fucose, sialic acid, N-acetyl glucosamine and N-acetyl galactosamine.

The present phospholipid-saccharide conjugates may be obtained by a variety of methods suitable for forming phospholipid-saccharide conjugates, including enzymatic and chemical processes. In a preferred embodiment, the present phospholipid-saccharide conjugates are formed by covalent conjugation of a phospholipid derivative and an activated saccharide derivative. The phospholipid derivative preferably is a hydroxy-functional derivative obtained via chemical or enzymatic coupling between a phospholipid and an alcohol. Preferred starting phospholipids include dimyristoyl, dipalmitoyl, distearoyl, dioleoyl and palmitoyl oleoyl phospholipids. In one embodiment of the invention, the phospholipid derivative is generated by transphosphatidylation of a phospholipid to a diol using a phospholipase-D (PL-D) enzyme isolated from *Streptomyces flavopersicum*. The diol has the general structure HO—X—OH wherein X is as defined above. In a particularly preferred embodiment, X comprises an alkyl having the formula $(CH_2)_n$ wherein n is an integer in the range of from about 1 to about 16.

The activated saccharide derivative used in producing the phospholipid-saccharide conjugate of this invention may be a monosaccharide, disaccharide, oligosaccharide or polysaccharide which has been activated at the $C_1$ position using standard chemical manipulations. For example, the activated saccharide derivative may be a glycosyl halide such as those described by H. Paulsen in *Angew. Chem. Int. Ed.*, 21:155–224 (1982); a glycosyl imidate such as those described by R. R. Schmidt and J. Michel in *J. Carbo. Chem.*, 4:141–169 (1985); a thio-glycoside such as those described by P. Fugedi et al. in *Glycoconjugate J.*, 4:97–108 (1987); an alkenyl glycoside such as those described by B. Fraser-Reid et al. in *J. C. S. Chem. Comm.*, 823–825 (1988) or an oxazoline as described by M. Colon et al. in *Tet. Letters*, 32:4447–4450 (1991). The remaining hydroxyl groups on the saccharide molecule may be blocked by protecting groups or may be replaced by an amide functional group, if desired.

In one embodiment of the present process, the conjugate is produced by combining the phospholipid derivative, the activated saccharide derivative and a coupling reagent in an organic solvent medium. The coupling reagent used depends on the activating group on the saccharide derivative. Useful coupling agents include, for example, silver salts, mercuric salts, and cadmium carbonate for glycosyl halides; Lewis acids for glycosyl imidates and oxazolines; dimethyl(methylthio)sulfonium trifluoromethane sulfonate for thioglycosides; and iododicollidine perchlorate for alkenyl glycoside. The organic solvent medium is selected to be compatible with the phospholipid, the activated saccharide derivative and the coupling reagent. The coupling reaction is allowed to proceed at a temperature and for a time sufficient to permit covalent conjugation between the saccharide and phospholipid moieties.

Phospholipid-saccharide conjugates according to the invention can be used to produce liposomes. Liposomes formed from the present conjugates may exhibit enhanced resistance to RES uptake in vivo. In addition, phospholipid-saccharide liposomes can be designed to target a specific tissue or cell type. For example, liposomes which are specific for a cell type having a sugar receptor (e.g., a mannose receptor) can be formed using phospholipid-sugar conjugates made by covalent conjugation of a hydroxy-functional phospholipid derivative and an activated mannose molecule. Upon administration to a mammal in vivo, the resulting liposomes may be specific for cells or tissues having the mannose receptor, such as liver cells. Alternatively, liposomes prepared from phospholipid-saccharide conjugates may be designed to prevent uptake by RES. For example, sialic acid has a negatively charged moiety on the sugar ring. Therefore, liposomes prepared using sialic acid-phospholipids would not be readily taken up by the RES. Optionally, a drug or other agent may be incorporated into or attached to the liposome, which can be used to deliver the drug or agent to a specific tissue and/or to facilitate transport of the drug or agent across the cell membrane.

DETAILED DESCRIPTION

The phospholipid-saccharide conjugates according to the invention comprise a phospholipid and a saccharide joined by a diether linker. The term "phospholipid" as used herein refers to a class of compounds having a glycerol backbone which is acylated at the $C_1$ and $C_2$ positions with a lipid moiety and in which the $C_3$ position is a phosphoric acid ester. Naturally occurring phospholipids (phosphatides) possess fatty acid residues at the $C_1$ and $C_2$ positions, and typically contain an alcohol and a functional group in the phosphate head group. Exemplary phospholipids include phosphatidylcholine, phosphatidic acid, phosphatidylserine, phosphatidylethanolamine, phosphatidylinositol and phosphatidylglycerol.

The term "saccharide" refers to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Exemplary monosaccharides include glucose, mannose, xylose, galactose fucose, fructose, sialic acid, N-acetyl glucosamine and N-acetyl galactos-amine. Disaccharides contain 2 such units joined by a glycosidic linkage. Disaccharides include, for example, sucrose, lactose, maltose and cellobiose. Oligosaccharides typically contain from 2 to 10 monosaccharide units joined in glycosidic linkage. Polysaccharides (glycans) typically contain more than 10 such units. The term "sugar" generally refers to mono-, di- or oligosaccharides.

The phospholipid-saccharide conjugates of the present invention have the following structure:

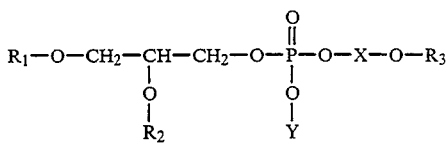

wherein $R_1$, $R_2$, $R_3$, X and Y are as defined hereinabove.

A preferred process for making the present conjugates also is the subject of the present invention. The process involves covalent conjugation of a phospholipid derivative and an activated sugar. The phospholipid derivative comprises a hydroxy-functional phospholipid having the general formula

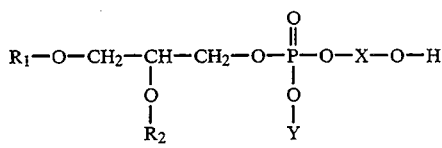

wherein $R_1$, $R_2$, X and Y are as defined hereinabove. The phospholipid derivative may be obtained via chemical or enzymatic coupling between a phospholipid and an alcohol. Phospholipids which are useful as starting material in the chemical or enzymatic coupling reaction include, for example, phosphatidylcholine, phosphatidic acid, phosphatidylserine, phosphatidylethanolamine, phosphatidylinositol, phosphatidylglycerol or combinations thereof. Particularly preferred phospholipids include dimyristoyl, dipalmitoyl, distearoyl, dioleoyl and palmitoyl oleoyl phospholipids. The alcohol may be any hydroxy-functional compound which can react with the phosphate group to form a stable hydroxy-functional intermediate. The alcohol preferably is a diol having the general structure HO-X-OH, wherein X is as defined above, and preferably contains at least one primary hydroxy group. The ratio of the phospholipid to the diol (or other alcohol) preferably is in the range of from about 1:25 to about 1:100.

In one preferred embodiment of the present process, the phospholipid derivative is generated by enzyme-catalyzed transphosphatidylation of a phospholipid to a diol using a phospholipase-D (PL-D) enzyme isolated from *Streptomyces flavopersicum* (*S. flavopersicum*). The PL-D enzyme used in the reaction may be crude enzyme extract, or may be purified, for example, by standard chromatographic techniques. An *S. flavopersicum* enzyme preparation which is particularly useful for this purpose can be obtained, for example from Genzyme Corporation (Cambridge, Mass.). The enzyme optionally may be immobilized on a solid support. Immobilization allows for repeated use of the enzyme and may render the procedure more cost effective.

The enzymatic reaction may be carried out in an aqueous buffer containing detergents, or preferably, in a biphasic system comprising aqueous buffers and organic solvents. Useful organic solvents include, but are not limited to, ethers such as tert-butylmethylether, diethylether, and acetonitrile. The aqueous buffer should be kept at the optimal pH for the particular PL-D enzyme, which usually lies between about 5 and 7. The molarity of the buffer system preferably is in the range of from about 0.1 to about 1.0 M. The ratio of organic solvent to aqueous buffer may be in the range from about 1:1 to about 4:1 (v/v). For the PL-D enzyme isolated from *S. flavopersicum*, a solvent mixture composed of a 2:1 ratio of tert-butylmethylether and 0.04 M calcium acetate-acetic acid buffer at pH 6.4 is particularly preferred.

The reaction is carried out at a temperature and for a time sufficient to ensure that transphosphatidylation is complete. Generally, a temperature ranging from ambient temperature (e.g., 18°-22° C.) to about 50° C. for about 16 to about 48 hours, is sufficient. The phospholipid derivative then can be isolated using standard techniques known to those skilled in the art. For example, the organic phase of the reaction mixture may be removed by concentration under reduced pressure and the resulting aqueous phase extracted with a mixture of chloroform/methanol. The chloroform/methanol layer then may be concentrated under reduced pressure and the desired phospholipid derivative isolated by precipitation with acetone, usually in yields greater than 80%.

The activated sacharide derivative used in producing the phospholipid-saccharide conjugate of this invention may be a monosaccharide, a disaccharide or an oligosaccharide which has been activated at the $C_1$ position using standard chemical manipulations. For example, the activated saccharide derivative may be a glycosyl halide, glycosyl imidate, thio-glycoside, or an alkenyl glycoside. The remaining hydroxyl groups on the saccharide molecule may be blocked by protecting groups such as esters or benzyl ethers, or may be replaced by an amide functional group.

To produce the phospholipid-saccharide conjugates of the present invention, the phospholipid derivative, the activated saccharide derivative and a coupling reagent are mixed in an organic solvent medium. The coupling reagent used depends on the activating group on the saccharide derivative. Useful coupling agents include, for example, silver salts, mercuric salts, and cadmium carbonate for glycosyl halides; Lewis acids for glycosyl imidates and oxazolines; dimethyl(methylthio)sulfonium trifluoromethane sulfonate for thioglycosides; and iododicollidine perchlorate for alkenyl glycosides. The solvent medium is selected to be compatible with the phospholipid, the activated saccharide derivative and the coupling reagent. Organic solvents which are useful include, for example, toluene, nitromethane, chloroform, methanol and mixtures of these solvents. The coupling reaction is allowed to proceed until complete, generally at a temperature of from about −20° C. to about 70° C. for about 16 to 48 h. For example, a mixture of 1-chloro-1-deoxy-2,3,46-tetra-O-benzylgalactose, phosphatidyl-1,3-propandiol, and cadmium carbonate in nitromethane/toluene stirred at reflux for 18 hours yields the corresponding phospholipid-saccharide conjugate.

Once the reaction is complete, the phospholipid-saccharide conjugate can be isolated and purified by standard techniques including, for example, silica gel chromatography, crystallization, or precipitation by acetone. The blocking groups of the saccharide moiety of the isolated phospholipid-saccharide derivative then can be removed using procedures known to those skilled in the art; for example, hydrogenolysis with $Pd/H_2/HCOOH$ can be used to remove benzyl ether blocking groups from the saccharide.

Phospholipid-saccharide conjugates made according to the present invention are particularly useful for making liposomes. Liposomes typically are formed from water-insoluble polar lipids in the presence of excess water. The highly ordered assemblages are arranged in a system of concentric closed membranes of an unbroken biomolecular sheet of lipid molecules which are separated from each other by water molecules. Methods for making liposomes using phospholipid-saccharide conjugates are well known and do not form a part of this invention. Liposomes may be prepared by a variety of techniques (see, for example, F. Szoka et al (1980) *Ann. Rev. Biophys. Bioeng.*, 9:467; J. Willschut in *Liposome Methodology*, L. E. Laserman and J Barbet (eds) INSERM, Paris, p. 11 (1982)). Preparation of liposomal vesicles from galactosylated lipids using a reversed phase evaporation technique is described by J. Haensler et al. in *Glycoconjugate J.*, 8:116–124 (1991).

Liposomes made using the present phospholipid-saccharide conjugates have several advantages. For example, since the saccharide is coupled to a component of the lipid vesicle prior to its formation, any non-specific or non-covalent adhesion of free saccharide to the vesicle is eliminated. Secondly, the percentage of the saccharide within the liposome formulation is fixed before the liposome is formed, thus allowing a defined proportion of saccharide in the resultant lipid.

Liposomes containing phospholipid-saccharide conjugates of the present invention can be used to deliver a drug or other agent in vivo. The drug or agent may be incorporated into the liposome, e.g., during its formation, or may be attached to the liposome after its formation. The liposomes may protect the drug or agent from degradation in vivo and/or to facilitate transport of the drug or agent across the cellular membrane. Liposomes incorporating the present phospholipid-saccharide conjugates as described herein can be designed to target a specific cell type or tissue, for example, either by selecting the sugar moiety of the conjugate to interface with a cellular sugar receptor, or by incorporating into the liposome an antibody, protein or other determinant which is specific for a cell-surface receptor on the targeted cell type or tissue. For example, many mammalian cells including hepatocytes and macrophages contain cell-surface lectins which specifically bind galactose residues (J. Haensler et al., ibid.). Liposomes bearing galactosyl ligands can be prepared which specifically target these cells. A drug or other agent can be incorporated into a targeted liposome, as described above, and can thus be delivered to a specific cells or tissues.

The present phospholipid-saccharide conjugates also may be used as in bioassy applications, for example, as ligands to study the antigenicities and receptor functions of carbohydrate chains of glycoproteins, as described by P. W. Tang et al. (*Biochem. & Biophys. Res. Comm.*, 132:474–480 (1985)) and T. Mizuochi et al. (*J. Biol. Chem.*, 264:13834–13839 (1989)). For this purpose, the phospholipid-saccharide conjugates may be coated on plates and their binding to monoclonal antibodies and lectins assessed by binding or inhibition assays.

The invention will be further illustrated by the following non-limiting examples.

EXAMPLES

EXAMPLE 1

Transesterification of Distearoyl Phosphatidylcholine with 1,3-propanediol

To a solution of distearoyl phosphatidylcholine (Avanti, 3.00 g, 3.80 mmol) in 300 ml of t-butyl methyl ether was added 1,3-propanediol (Aldrich, 15.01 g, 197.20 mmol) dissolved in 0.04M calcium acetate buffer (150 ml, pH 6.4) and 25 units of PL-D enzyme (Sigma).

The solution was stirred at 45°–50° C. for 16 h. Thin layer chromatography analysis of the reaction mixture (65:35:5 chloroform/methanol/water, visualized by molybdenum blue reagent) indicated that all the phosphatidylcholine (Rf value: 0.50) had reacted and that a new phospholipid derivative (Rf value: 0.80) had formed. The reaction mixture was concentrated at reduced pressure to give an aqueous suspension. To this was added 1:1 chloroform/methanol (200 ml) and the mixture was heated to reflux whereupon the organic layer was separated while still warm. The organic layer was concentrated at reduced pressure to approximately one-third volume and a 1:1 methanol/acetone mixture was (200 ml) was added to give a white precipitate. The heterogeneous mixture was allowed to stand for thirty minutes at room temperature. The precipitate was collected by filtration and washed with acetone (25 ml). The solid collected was then dried under high vacuum to give distearoyl phosphatidyl propanediol (DSP-propanediol, 2.68 g, 87%). $^1$H NMR data (3:1CDCl$_3$/MeOH-d$_4$): $\delta$5.06 (m, 1H), 4.23 (dd, 1H), 4.01 (dd, 1H), 3.78 (t,2H), 3.67 (q,2H), 3.42 (t,2H), 2.15 (m,4H), 1.39 (m,2H), 1.19 (br.s,60H), 0.73 (t,6H).

EXAMPLE 2

Transesterification of Distearoyl Phosphatidylcholine with 1,5-pentanediol

To a solution of distearoyl phosphatidylcholine (Avanti, 3.00 g, 3.80 mmol) in 300 ml of t-butyl methyl ether was added 1,5-pentanediol (Aldrich, 19.77 g, 0.1898 mol) and 25 units of PL-D enzyme was used, as described in Example 1, to give a new phospholipid derivative (Rf value: 0.80 vs 0.41). The precipitate was collected by filtration and washed with acetone (25 ml). The solid collected was then dried under high vacuum to give distearoyl phosphatidyl pentanediol (DSP-pentanediol, 2.94 g, 92%). $^1$H NMR data (3:1CDCl$_3$/MEOH-d$_4$): $\delta$5.08 (m, 1H), 4.25 (dd, 1H), 4.03 (dd, 1H), 3.81 (t,2H), 3.72 (q,2H), 3.46 (t,2H), 2.17 (m,4H), 1.46 (m,4H), 1.33 (m,2H), 1.13 (br.s,60H), 0.75 (t,6H).

EXAMPLE 3

Transesterification of Distearoyl Phosphatidylcholine with 1,8-octanediol

To a solution of distearoyl phosphatidylcholine (Avanti, 3.00 g, 3.80 mmol) in 300 ml of t-butyl methyl ether was added 1,8-octanediol (Aldrich, 27.76 g, 0.1898 mol) and 25 units of PL-D enzyme was used, as in Example 1, to give a new phospholipid derivative (Rf value: 0.88 vs 0.47). The precipitate was collected by filtration and washed with acetone (25 ml). The solid collected was then dried under high vacuum to give distearoyl phosphatidyl octanediol (DSP-octanediol, 3.06 g, 91%). $^1$H NMR data (3:1CDCl$_3$/MEOH-d$_4$): $\delta$5.06 (m, 1H), 4.23 (dd, 1H), 4.01 (dd, 1H), 3.78 (t,2H), 3.67 (q,2H), 3.42 (t,2H), 2.15 (m, 1H), 1.39 (m,4H), 1.17 (br.s,8H), 1.12 (br.s,60H), 0.73 (t,6H).

EXAMPLE 4

Transesterification of Dipalmitoyl Phosphatidylcholine with 1,3-propanediol

To a solution of dipalmitoyl phosphatidylcholine (Genzyme, 3.00 g, 4.09 mmol) in 300 ml of t-butyl methyl ether was added 1,3-propanediol (Aldrich, 15.55 g, 0.2043 mol) and 25 units of PL-D enzyme was used, as in Example 1, to give a new phospholipid derivative (Rf value: 0.58 vs 0.28). The precipitate was collected by filtration and washed with acetone (25 ml). The solid collected was then dried under high vacuum to give dipalmitoyl phosphatidyl propanediol (DPP-propanediol, 2.75 g, 89%). $^1$H NMR data (3:1CDCl$_3$/MeOH-d$_4$): $\delta$65.07 (m,1H), 4.24 (dd, 1H), 4.02 (dd, 1H), 3.82 (q,2H), 3.58 (t,2H), 2.16 (m,4H), 1.64 (m,2H), 1.11 (br.s,52H), 0.73 (t,6H).

EXAMPLE 5

Perbenzylation of methyl-$\beta$-D-glucopyranoside

A general procedure according to S. Koto et al. (*Bull. Chem. Soc. Japan*, (1976), 49:2939–40) was followed. A suspension of methyl-$\alpha$-D-glucopyranoside (Aldrich, 5.02 g, 0.0259 mol), sodium hydride (Aldrich, 4.31 g, 0.1796 mol) and benzyl chloride (Aldrich, 125 ml, 25:1 (v/w) vs carbohydrate) was stirred vigorously and heated to a bath temperature of 115° C. whereupon the gray reaction mixture thickened and an exotherm occurred. The reaction mixture reached 135° C. and turned into a thin, yellowish slurry. The reaction was allowed to stir at this temperature for 1 h. The insoluble material was removed by filtration and the solution concentrated in vacuo. Flash chromatography on silica gel (E. M. Science, 230–400 mesh) using methylene chloride as eluant gave the product (Rf value: 0.63) as an oil (7.45 g, 52%). $^1$H NMR data (CDCl$_3$): $\delta$7.27 (m, 20H, aromatic H on benzyl group), 3.45 (s, 3H, —OC$\underline{H}_3$).

EXAMPLE 6

Perbenzylation of Methyl-$\beta$-D-galactopyranoside

Methyl-$\beta$-D-galactopyranoside (Aldrich, 5.40 g, 0.0278 mol) was reacted and purified as in Example 5 to give the product (Rf value: 0.50) as an oil (10.85 g, 70%). Selected $^1$H NMR data (CDCl$_3$): $\delta$7.28 (m,20H, aromatic H on benzyl group), 3.55 (s,3H, —OC$\underline{H}_3$).

EXAMPLE 7

Perbenzylation of methyl-$\alpha$-D-mannopyranoside

Methyl-$\alpha$-D-mannopyranoside (Aldrich, 5.40 g, 0.0278 mol) was reacted and purified as in Example 5 to give the product (Rf value: 0.64) as an oil (10.89 g, 71%). Selected $^1$H NMR data (CDCl$_3$): $\delta$7.27 (m,20H, aromatic H on benzyl group), 3.32 (s,3H, —OC$\underline{H}_3$).

EXAMPLE 8

Perbenzylation of methyl-galactosyl-($\beta$1-4)-glucopyranoside

Methyl-galactosyl-($\beta$1,4)-glucopyranoside (5.40 g, 0.0278 mol) was reacted and purified as in Example 5 to give the product (Rf value: 0.55) as an oil (1.16 g, 8%). Selected $^1$H NMR data (CDCl$_3$): $\delta$7.26 (m,35H, aromatic H on benzyl group), 3.37 (s,3H, —OC$\underline{H}_3$).

EXAMPLE 9

Synthesis of 2,3,4,6-tetra-O-benzyl-glucopyranoside

A general procedure according to S. Koto et al. (*Bull. Chem. Soc. Japan*, ibid.) was followed. Methyl-2,3,4,6-tetra-O-benzyl glucopyranoside (7.42 g, 0.0134 mol) was dissolved in acetic acid (85 ml). To the homogeneous mixture was added 6N hydrochloric acid (15 ml). The reaction mixture was heated to 85° C. for 30 minutes. At this point the reaction mixture was poured over ice (200 g) and extracted with toluene (2×75 ml). The combined organic layers were then washed with saturated sodium bicarbonate (3×25 ml) and water (25 ml), dried over sodium sulfate and concentrated to a yellow solid. The solid was recrystallized from toluene to give a white solid (1.47 g, 20%) (Mp 141°–144° C.; lit. mp 148° C.).

EXAMPLE 10

Synthesis of 2,3,4,6-tetra-O-benzyl-galactopyranoside

Methyl-2,3,4,6-tetra-O-benzyl-galactopyranoside (10.85 g, 0.0196 mol) was dissolved in acetic acid (100 ml). To the homogenous mixture was added 3N sulfuric acid (15 ml). The reaction mixture was heated to 85° C. for 40 minutes. At this point the reaction mixture was poured over ice (200 g) and extracted with toluene (2×75 ml). The combined organic layers were then washed with saturated sodium bicarbonate (3×25 ml) and water (25 ml), dried over sodium sulfate and concentrated to give an amber syrup. Flash chromatography on silica gel (E. M. Science, 230–400 mesh) using 40:1 chloroform/methanol as eluant gave the product (Rf value: 0.30) as a syrup (3.44 g, 33%).

EXAMPLE 11

Synthesis of 2,3,4,6-tetra-O-benzyl-mannopyranoside

Methyl-2,3,4,6-tetra-O-benzyl-mannopyranoside (10.89 g, 0.0196 mol) was dissolved in acetic acid (100 ml) and treated as in Example 10 to give an amber syrup. Flash chromatography on silica gel (E. M. Science, 230–400 mesh) using 40:1 chloroform/methanol as eluant gave the product (Rf value: 0.33) as a syrup (3.10 g, 30%).

EXAMPLE 12

Synthesis of 1-hydroxy-hepta-O-benzyl-lactose

Methy-2,3,4,6-tetra-O-benzyl-galactosyl-($\beta$1-4)-2,3,6-tri-O-benzyl-glucopyranoside (1.16 g,0.0012 mol) was dissolved in acetic acid (80 ml) and treated as in Example 10 to give an amber syrup. Flash chromatography on silica gel (E. M. Science, 230–400 mesh) using 40:1 chloroform/methanol as eluant gave the product (Rf value: 0.32) as a syrup (696 mg, 61%).

EXAMPLE 13

Synthesis of $\alpha$-1-chloro-perbenzyl-glucopyranoside

A procedure according to T. Iverson and D. R. Bundle was followed (*Carbohydr. Res.*, (1982), 103:29–40). 2,3,4,6-Tetra-O-benzyl-glucopyranoside (440 mg, 0.81 mmol) was dissolved in methylene chloride (5 ml) to which N,N-dimethylformamide (Aldrich, 200 $\mu$l ) had been added. Oxalyl chloride (Aldrich, 2.0 M in methylene chloride, 1.22 ml, 2.44 mmol) dissolved in methylene chloride (3 ml) was added dropwise. The mixture was allowed to stir at room temperature under a nitrogen atmosphere for 16 h. Thin layer chromatography analysis on silica gel (methylene chloride, visualized by 5% sulfuric acid in ethanol char and UV) indicated that all of the carbohydrate had been consumed (Rf value: 0.38) and a new carbohydrate derivative had formed (Rf value: 0.93). The reaction mixture was concentrated under reduced pressure to give an oil. A mixture of 1:1 (v/v) of hexane/ethyl acetate (20 ml) was added to the oil to give a heterogeneous mixture which was then filtered through a plug of silica gel. The organic solution was then concentrated under reduced pressure to give an oil which was dried under vacuum (444 mg, 97%).

EXAMPLE 14

Synthesis of α-1-chloro-perbenzyl-galactopyranoside 2,3,4,6-Tetra-O-benzyl-galactopyranoside (635 mg, 1.18 mmol) was treated as in Example 13 to give the product as an oil (417 mg, 64%).

EXAMPLE 15

Synthesis of α-1-chloro-perbenzyl-mannopyranoside 2,3,4,6-Tetra-O-benzyl-mannopyranoside (640 mg, 1.18 mmol) was treated as in Example 13 to give the product as an oil (525 mg, 88%)

EXAMPLE 16

Synthesis of α-1-chloro-perbenzyl-lactose 2,3,4,6-Tetra-O-benzyl-galactosyl-(β1-4)-2,3,6-tri-O-benzyl-glucopyranoside (675 mg, 0.68 mmol) was treated as in Example 13 to give the product as an oil (503 mg, 73%).

EXAMPLE 17

Coupling of DSP-propanediol with α-1-chloro-2,3,4,6-tetra-O-benzyl-glucopyranoside α-1-Chloro-2,3,4,6-tetrabenzyl-glucopyranoside (136 mg, 0.24 mmol) was dissolved in a 1:1 (v/v) mixture of toluene/nitromethane (3 ml) and added to a heterogeneous solution of distearoyl phosphatidyl propanediol (177 mg, 0.22 mmol) in 1:1 toluene/nitromethane (15 ml). To this was added calcium sulfate (Drierite,0.5 g) and cadmium carbonate (Aldrich, 41.8 mg, 0.24 mmol) and the reaction was heated to reflux and allowed to stir under a nitrogen atmosphere for 64 h. Thin layer chromatography analysis on silica gel (10:1 chloroform/methanol, visualization by both molybdenum blue reagent and 5% sulfuric acid char) indicated a new carbohydrate derivative (Rf value: 0.26 vs 0.98) which was also a new phospholipid derivative (Rf value: 0.26 vs 0.00). The reaction mixture was filtered through a plug of celite while hot to rid of all inorganic materials and the organic solution was concentrated in vacuo to give an oil. The compound was purified by flash chromatography on silica gel (40:1(v/v) chloroform/methanol) to give a syrup which was dried under high-vacuum (91 mg,32%). Selected $^1$H NMR data (CDCl$_3$): δ7.26 (br.s,20H, aromatic H on benzyl groups), 5.27 (m, 1H, (sn-2) C$\overline{\text{H}}$), 2.22 (m,4H, O—(O)—C—C$\overline{\text{H}}$), 1.92 (m,2H, —O—C$\overline{\text{H}}_2$CH$_2$CH$_2$—O—), 1.24 (br.s,$\overline{60}$H, fatty acyl chain), 0.86 (t,6H,CH$_3$).

EXAMPLE 18

Coupling of DSP-propanediol with α-1-chloro-2,3,4,6-tetra-O-benzyl-galactopyranoside α-1-Chloro-2,3,4,6-tetrabenzyl-galactopyranoside (230 mg, 0.41 mmol) and distearoyl phosphatidyl propanediol (165 mg, 0.21 mmol) were reacted as in Example 17. Thin layer chromatography analysis on silica gel (10:1 chloroform/methanol, visualization by both molybdenum blue reagent and 5% sulfuric acid char) indicated a new carbohydrate derivative (RF value: 0.23 vs 0.95) which was also a new phospholipid derivative (Rf value: 0.23 vs 0.00). The product was isolated and purified as in Example 17 to give a syrup which was dried under high-vacuum (38 mg, 14%). Selected $^1$H NMR data (CDCl$_3$): δ7.28 (br.s,20H, aromatic H on benzyl groups), 5.22 (m, 1H,(sn-2)C$\overline{\text{H}}$), 2.18 (m,4H, O—(O)—C—CH$_2$—), 1.50 (m,2H, —O—CH$_2$CH$_2$CH$_2$—O—), 1.26 (br.s,60H, fatty acyl chain), 0.89 (t,$\overline{6}$H,CH$_3$).

EXAMPLE 19

Coupling of DSP-propanediol with α-1-chloro-2,3,4,6-tetra-O-benzyl-mannopyranoside α-1-Chloro-2,3,4,6-tetrabenzyl-mannopyranoside (230 mg, 0.41 mmol) and distearoyl phosphatidyl propanediol (165 mg, 0.21 mmol) were reacted as in Example 17. Thin layer chromatography analysis on silica gel (10:01 chloroform/methanol, visualization by both molybdenum blue reagent and 5% sulfuric acid char) indicated a new carbohydrate derivative (RF value: 0.24 vs 0.93) which was also a new phospholipid derivative (Rf value: 0.24 vs 0.00). The product was isolated and purified as in Example 17 to give a syrup which was dried under high-vacuum (76 mg, 28%). Selected $^1$H NMR data (CDCl$_3$): δ7.26 (br.s,20H, aromatic H on benzyl groups), 5.28 (m, 1H,(sn-2)C$\overline{\text{H}}$), 2.21 (m, 4H, O—(O)—C—CH$_2$—), 1.81 (m, H, —O—CH$_2$CH$_2$CH$_2$—O—), 1.23 (br.s,60H, fatty acyl chain), 0.88 (t,$\overline{6}$H,CH$_3$).

EXAMPLE 20

Coupling of DSP-propanediol with α-1-chloro-2,3,4,6-tetra-O-benzyl-galactosyl-(β1,4)-2,3,6 tri-O-benzyl-glucopyranoside α-1-Chloro-2,3,4,6-tetrabenzyl-galactopyranosyl-(β1,4)-2,3,6-tri-O-benzyl-glucopyranoside (260 mg, 0.26 mmol) were reacted as in phosphatidyl propanediol (165 mg, 0.21 mmol) were reacted as in Example 17. Thin layer chromatography analysis on silica gel (10:1 chloroform/methanol, visualization by both molybdenum blue reagent and 5% sulfuric acid char) indicated a new carbohydrate derivative (Rf value: 0.10 vs 0.96) which was also a new phospholipid derivative (Rf value: 0.33 vs 0.00). The product was isolated and purified as in Example 17 to give a syrup which was dried under high-vacuum (124 mg, 40%). Selected $^1$H NMR data (CDCl$_3$): δ7.27 (br. s, 35H, aromatic H on benzyl groups), 5.30 (m, 1H,(sn-2)C$\overline{\text{H}}$), 2.22 (m, 4H, O—(O)—C—CH$_2$—), 1.90 (m,2H,—OCH$_2$—CH$_2$CH$_2$—O—), 1.21 (br. s, 60H, fatty acyl chain), 0.90 (t, 6H, CH$_3$).

EXAMPLE 21

Coupling of DSP-octanediol with α-1-chloro-2,3,4,6-tetra-O-benzyl-mannopyranoside α-1-Chloro-2,3,4,6-tetrabenzyl-mannopyranoside (2.37 g, 0.0042 mol) was dissolved in a 1:1 (v/v) mixture of toluene/nitromethane (10 ml) and added to a heterogeneous solution of distearoyl phosphatidyl octanediol (2.51 g,0.0028 mol) in 1:1 toluene/nitromethane (60 ml). To this was added calcium sulfate (Drierite, 2.5 g) and cadmium carbonate (Aldrich, 731 mg, 0.0042 mol) and the reaction heated to reflux and allowed to stir under a nitrogen atmosphere for 64 h. Thin layer chromatography analysis on silica gel (10:1 chloroform/methanol, visualization by both molybdenum blue reagent and 5% sulfuric acid char) indicated a new carbohydrate derivative (Rf value: 0.24 vs 0.98) which was also a new phospholipid derivative (Rf value: 0.24 vs 0.00). The reaction mixture was filtered through a plug of celite while hot to remove inorganic materials and the organic solution was concentrated in vacuo to give an oil. The product was purified by flash chromatography on silica gel (40:1 (v/v) chloroform/methanol) to give a syrup which was dried under high-vacuum (831 mg, 21%). Selected $^1$H NMR data (CDCl$_3$): δ7 7.27 (br.s,20H, aromatic H on benzyl groups), 5.35 (m, 1H,(sn-2)C$\underline{H}$), 2.28 (m,4H,O—(O)—C—C$\underline{H_2}$—), 1.26 (br.s,60H, fatty acyl chain), 0.89 (t, 6H, C$\underline{H_3}$).

EXAMPLE 22

Coupling of DSP-octanediol with α-1-chloro-2,3,4,6-tetra-O-benzyl-galactopyranoside α-1-Chloro-2,3,4,6-tetra-O-benzyl-galactopyranoside (2.98 g,0.0053 mol) and distearoyl phosphatidyl octanediol (3.60 g, 0.0041 mol) were reacted as in Example 21. Thin layer chromatography analysis on silica gel (10:1 chloroform/methanol, visualization by both molybdenum blue reagent and 5% sulfuric acid char) indicated a new carbohydrate derivative (Rf value: 0.28 vs 0.98) which was also a new phospholipid derivative (Rf value: 0.28 vs 0.00). The product was isolated and purified as in Example 21 to give a syrup which was dried under high-vacuum (3.01 g, 53%). Selected $^1$H NMR data (CDCl$_3$): δ7.26 (br.s,20H, aromatic H on benzyl groups), 5.39 (m, 1H,(sn-2)C$\underline{H}$), 2.27 (m,4H, O—(O)—C—C$\underline{H_2}$), 1.25 (br. s, 60H, fatty acyl chain), 0.88 (t, 6H, C$\underline{H_3}$).

EXAMPLE 23

Coupling of DPP-propanediol with α-1-chloro-2,3,4,6-tetra-O-benzyl-mannopyranoside α-1-Chloro-2,3,4,6-tetra-O-benzyl-mannopyranoside (2.37 g, 0.0042 mol) and dipalmitoyl phosphatidyl propanediol (2.15 g, 0.0028 mol) were reacted as in Example 17. Thin layer chromatography analysis on silica gel (10:1 chloroform/methanol, visualization by both molybdenum blue reagent and 5% sulfuric acid char) indicated a new carbohydrate derivative (Rf value: 0.25 vs 0.96) which was also a new phospholipid derivative (RF value: 0.25 v 0.00). The product was isolated and purified as in Example 17 to give a syrup which was dried under high-vacuum (1.12 g, 31%). Selected $^1$H NMR data (CDCl$_3$): δ7.28 (br.s,20H, aromatic H on benzyl groups), 5.25 (m, 1H,(sn-2)C$\underline{H}$), 2.21 (m,4H, O—(O)—C—C$\underline{H_2}$—), 1.62 (m,2H, —O—C$\underline{H_2}$C$\underline{H_2}$CH$_2$—O—), 1.26 (br.s,52H, fatty acyl chain), 0.88 (t,6H,CH$_3$).

EXAMPLE 24

Synthesis of distearoyl phosphatidyl-propyl-glucopyranoside

A general procedure for transfer hydrogenation by B. El Amin et al. (*J. Org. Chem.*, (1979) 44:3442-4) was followed. Palladium black (Aldrich, 99.0 mg) was added to a 4.4% solution of formic acid in methanol (2 ml). To this was added a solution of the distearoyl phosphatidyl propyl-2,3,4,6-tetra-O-benzyl-glucopyranoside (36.3 mg, 0.03 mmol) in 1:1 (v/v) methanol/chloroform (1 ml). The reaction was allowed to stir at room temperature for 16 h. Thin layer chromatography analysis on silica gel (65:35:5 chloroform/methanol/water, visualized by molybdenum blue reagent and 5% sulfuric acid char) indicated complete consumption of the starting carbohydrate/phospholipid (Rf value: 0.92) and that a new carbohydrate/phospholipid derivative had formed (Rf value: 0.65). The reaction was filtered through a plug of celite to remove the spent catalyst and concentrated at reduced pressure. The residue was dissolved in 3:1 chloroform/methanol (1 ml) and acetone was added (25 ml) to give a white precipitate. The mixture was allowed to stand for 15 minutes. The precipitate was collected by centrifugation washed with acetone and dried under high-vacuum, to give a white solid (23.3 mg, 90%). $^1$H NMR data (3:1CDCl$_3$/MeOH-d$_4$): δ5.05 (m, 1H), 4.68 (d, 1H), 4.18 (dd, 1H), 3.84 (m,4H), 3.69 (t,1H), 3.53 (m,2H), 3.38 (m, 1H), 3.30 (m, 1H), 3.12 (m, 1H), 2.14 (m,4H), 1.75 (m,2H), 1.09 (br.s,60H), 0.71 (t,6H).

EXAMPLE 25

Synthesis of distearoyl phosphatidyl-propyl-galactopyranoside

The distearoyl phosphatidyl-propyl-2,3,4,6-tetra-O-benzyl-galactopyranoside (33 mg, 0.02 mmol) was reacted, isolated and purified as in Example 24 to give a new product (Rf value: 0.48 in 65:35:5 chloroform/methanol/water, visualized by molybdenum blue reagent and 5% sulfuric acid char) as a white solid (7 mg, 29%). $^1$H NMR data (3:1CDCl$_3$/MeOH-d$_4$): δ5.05 (m, 1H), 4.72 (d, 1H), 4.20 (dd, 1H), 4.09 (dd, 1H), 3.86 (m,4H), 3.63 (m,3H), 3.54 (m, 1H), 3.40 (m,2H), 2.14 (m,4H), 1.76 (m,2H), 1.08 (br.s,60H), 0.70 (t,6H).

EXAMPLE 26

Synthesis of distearoyl phosphatidyl-propyl-mannopyranoside

The distearoyl phosphatidyl-propyl-2,3,4,6-tetra-O-benzyl-mannopyranoside (38 mg, 0.03 mmol) was reacted, isolated and purified as in Example 24 to give a new product (Rf value: 0.56 in 65:35:5 chloroform/methanol/water, visualized by molybdenum blue reagent and 5% sulfuric acid char) as a white solid (15 mg, 54%). $^1$H NMR data (3:1CDCl$_3$/MeOH-d$_4$): δ5.02 (m, 1H), 4.58 (d,1H), 4.37 (dd,1H), 4.18 (dd,1H), 3.96 (m,1H), 3.85 (m,4H), 3.64 (m,1H), 3.56 (m,1H), 3.43 (m,2H), 3.31 (m,1H), 2.11 (m,4H), 1.71 (m,2H), 1.04 (br.s,60H), 0.67 (t,6H).

EXAMPLE 27

Synthesis of Distearoyl Phosphatidyl-propyl-galactosyl-(β1,4)-glucopyranoside

The distearoyl phosphatidyl-propyl-perbenzyl-lactopyranoside (105 mg, 0.06 mmol) was reacted, isolated and purified as in Example 24 to give a new product (Rf value: 0.58 in 65:35:5 chloroform/methanol/water, visualized by molybdenum blue reagent and 5% sulfuric acid char) as a white solid (47 mg, 69%). $^1$H NMR data (3:1CDCl$_3$/MeOH-d$_4$: δ5.06 (m,1H), 4.74 (d,1H), 4.20 (d,1H), 3.99 (m,2H), 3.94 (m,2H), 3.89 (m,4H), 3.67 (m,4H), 3.57 (m,1H), 3.47 (m,1H), 3.39 (m,1H), 3.17 (m,1H), 2.15 (m,4H), 1.77 (m,2H), 1.08 (br.s,6OH), 0.70 (t,6H).

EXAMPLE 28

Synthesis of distearoyl phosphatidyl-octyl-mannopyranoside

The distearoyl phosphatidyl-octyl-2,3,4,6-tetra-O-benzyl-mannopyranoside (830 mg, 0.59 mmol) was reacted, isolated and purified as in Example 24 to give a new product (Rf value: 0.53 in 65:35:5 chloroform/methanol/water, visualized by molybdenum blue reagent and 5% sulfuric acid char) as a white solid (360 mg, 58%). $^1$H NMR data (CDCl$_3$): δ5.17 (m,1H), 4.79 (d,1H),4.34 (dd, H), 4.11 (dd,1H), 3.90 (overlapping m, 4H,1H), 3.80 (m,2H), 3.71 (m,1H), 3.63 (m,1H), 3.51

(m,1H), 2.53 (br.s,6H), 2.24 (m,4H), 1.31 (br.s,6H), 1.20 (br.s,6OH), 0.83 (t,6H).

EXAMPLE 29

Synthesis of distearoyl phosphatidyl-octyl-galactopyranoside

The distearoyl phosphatidyl-octyl-2,3,4,6-tetra-O-benzyl-galactopyranoside (3.00 g, 0021 mol) was reacted, isolated and purified as in Example 24 to give a new product (Rf value: 0.45 in 65:35:5 chloroform/methanol/water, visualized by molybdenum blue reagent and 5% sulfuric acid char) as a white solid (785 mg, 35%). $^1$H NMR data (CDCl$_3$): δ5.16 (m,1H), 4.83 (d,1H), 4.32 (dd, 1H), 4.15 (dd,1H), 4.09 (m,1H), 3.94 (m,2H), 3.83 (m,2H), 3.75 (m,2H), 3.53 (br.m,3H), 2.99 (br.s,6H), 2.24 (m,4H), 1.29 (m,6H), 1.19(br.s,6OH), 0.82(t,6H).

EXAMPLE 30

Synthesis of dipalmitoyl phosphatidyl-propyl-mannopyranoside

The dipalmitoyl phosphatidyl-propyl-2,3,4,6-tetra-O-benzyl-mannopyranoside (1.13 g, 0.0009 mol) was reacted, isolated and purified as in Example 24 to give a new product (Rf value: 0.53 in 65:35:5 chloroform/methanol/water, visualized by molybdenum blue reagent and 5% sulfuric acid char) as a white solid (139 mg, 17%). $^1$H NMR data (CDCl$_3$/MeOH-d$_4$): δ5.06 (m, 1H), 4.71 (d, 1H), 4.18 (dd,1H), 3.82 (m,1H), 3.76 (m,1H), 3.69 (m,4H), 3.57 (m,1H), 3.51 (m,1H), 3.44 (m,1H), 3.36 (m,1H), 2.13 (m,4H), 1.72 (m,2H), 1.10 (br.s,52H), 0.72 (t,6H).

EQUIVALENTS

From the foregoing description, one skilled in the art can easily ascertain the essential characteristics of this invention and, without departing from the spirit and scope thereof, can make various changes and modifications to adapt it to various usages and conditions which are equivalent to the invention. Such equivalents are encompassed in the scope of the following claims.

What is claimed is:

1. A phospholipid-saccharide conjugate comprising the formula:

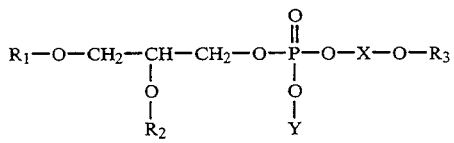

wherein R$_1$ and R$_2$ each independently comprise C(O)R wherein R comprises an alkyl, a substituted alkyl, an alkenyl, a substituted alkenyl, an alkynyl, a substituted alkynyl, an aryl, a substituted aryl, an aralykyl or a substituted aralkyl;

Y comprises a cation

X comprises an alkyl linker moiety of structure (CH$_2$)$_n$ wherein n is an integer in the range of 1 to about 16; and R$_3$ comprises a saccharide.

2. The phospholipid-saccharide conjugates of claim 1 wherein R$_1$ and R$_2$ comprise fatty acid residues.

3. The phospholipid-saccharide conjugates of claim 2 wherein R$_1$ and R$_2$ are fatty acid residues selected from the group consisting of myristoyl, palmitoyl, stearoyl and oleoyl.

4. The phospholipid-saccharide conjugates of claim 1 wherein Y is selected from the group consisting of a hydrogen ion, alkali metal ions, an ammonium ion and substituted ammonium ions.

5. The phospholipid-saccharide conjugates of claim 1 wherein R$_3$ is a monosaccharide, disaccharide, oligosaccharide or polysaccharide.

6. The phospholipid-saccharide conjugates of claim 5 wherein R$_3$ is selected from the group consisting of mannose, galactose, glucose, lactose, fucose, sialic acid, N-acetyl glucosamine and N-acetyl galactosamine.

7. The phospholipid-saccharide conjugates of claim 1 wherein said conjugate is formed by covalent conjugation of a phospholipid derivative and an activated saccharide.

8. A method for producing a phospholipid-saccharide conjugate of claim 1 comprising the steps of:
combining a hydroxyl-functional phospholipid derivative with an activated saccharide under conditions sufficient to form the phospholipid-saccharide conjugate.

9. The method of claim 8 wherein the combination further comprises a coupling reagent.

10. The method of claim 9 wherein said coupling reagent is selected from the group consisting of silver salts, mercuric salts, cadmium carbonate, Lewis acids, dimethyl(methylthio)sulfonium trifluromethane sulfonate and iododicollidine perchlorate.

11. The method of claim 8 wherein the hydroxyl-functional phospholipid derivative is formed by reaction of a phosphatidyl precursor with a diol.

12. The method of claim 11 wherein the phosphatidyl precursor is selected from the group consisting of phosphatidylcholine, phosphatidic acid, phosphatidylethanolamine, phosphatidylserine, phosphatidylinositol and phosphatidylglycerol.

13. The method of claim 12 wherein the phosphatidyl precursor is phosphatidylcholine or phosphatidic acid.

14. The method of claim 11 wherein the reaction is an enzyme-catalyzed transesterification reaction.

15. The method of claim 14 wherein the enzyme comprises phospholipase-D.

16. The method of claim 15 wherein the enzyme is isolated from *Streptomyces flavopersicum*.

17. The method of claim 8 wherein the activated saccharide comprises a saccharide having a reactive functional group in a C$_1$ position.

18. The method of claim 17 wherein the functional group is selected from the group consisting of halides, imidates, thio groups, and alkenyl groups.

* * * * *